(12) United States Patent
Corrigan et al.

(10) Patent No.: US 9,757,024 B2
(45) Date of Patent: Sep. 12, 2017

(54) OPHTHALMIC INSTRUMENT ARM ASSEMBLY HAVING DOGLEG LINK FOR EXTENDED REACH

(71) Applicant: RELIANCE MEDICAL PRODUCTS, INC., Mason, OH (US)

(72) Inventors: Sean J. Corrigan, Chicago, IL (US); Tomas Matusaitis, Chicago, IL (US); Keith A. Grider, Chicago, IL (US); Antonio Belton, Richton Park, IL (US)

(73) Assignee: Reliance Medical Products, Inc., Mason, OH (US)

(*) Notice: Subject to any disclaimer, the term of this patent is extended or adjusted under 35 U.S.C. 154(b) by 220 days.

(21) Appl. No.: 13/655,898

(22) Filed: Oct. 19, 2012

(65) Prior Publication Data
US 2013/0100411 A1    Apr. 25, 2013

Related U.S. Application Data

(60) Provisional application No. 61/548,968, filed on Oct. 19, 2011.

(51) Int. Cl.
*A61B 3/00* (2006.01)

(52) U.S. Cl.
CPC .................. *A61B 3/0083* (2013.01)

(58) Field of Classification Search
CPC ......... A61B 3/02; A61B 3/024; A61B 3/1015; A61B 3/18; A61B 3/00; A61B 3/0084; F16M 11/04; F16M 11/12; F16M 13/02

USPC ........... 351/225, 244, 245, 246; 248/123.11, 248/124.1, 183.1, 282.1
See application file for complete search history.

(56) References Cited

U.S. PATENT DOCUMENTS

| | | | |
|---|---|---|---|
| 2,491,242 A | 12/1949 | Alexander | |
| 4,695,024 A * | 9/1987 | Haven | 248/281.11 |
| 5,480,212 A | 1/1996 | Marconet | |
| 5,777,344 A | 7/1998 | Hayashi | |
| 5,907,387 A | 5/1999 | Schwaegerle | |
| 6,106,065 A | 8/2000 | Carroll | |
| 6,264,329 B1 * | 7/2001 | Brooks et al. | 351/221 |
| 6,575,575 B2 | 6/2003 | O'Brien et al. | |
| 7,461,825 B2 * | 12/2008 | Olivera | F16M 11/04 248/123.11 |
| 7,467,871 B2 * | 12/2008 | Lawhorn | A61B 3/0033 351/244 |
| 7,670,003 B2 | 3/2010 | Kendrick | |
| 2010/0069833 A1 * | 3/2010 | Wenderow | A61M 25/0113 604/95.01 |

* cited by examiner

*Primary Examiner* — Jie Lei
(74) *Attorney, Agent, or Firm* — Taft Stettinius & Hollister, LLP; Ryan O. White (57) ABSTRACT

An instrument arm assembly is provided for presenting an examination instrument to a seated patient. The instrument arm assembly includes an arm having an attachment assembly, an instrument supporting element for supporting the examination instrument and having an attachment assembly, and a linkage having first and second attachment assemblies. The instrument supporting element attachment assembly is pivotably connected with the linkage first attachment assembly, and the arm attachment assembly is pivotably connected with the linkage second attachment assembly.

16 Claims, 6 Drawing Sheets

FIG. 5D

OPHTHALMIC INSTRUMENT ARM ASSEMBLY HAVING DOGLEG LINK FOR EXTENDED REACH

RELATED APPLICATION

This application claims priority to U.S. Provisional Patent Application No. 61/548,968 filed Oct. 19, 2011, the disclosure of which is incorporated herein by reference in its entirety.

FIELD OF THE INVENTION

The present invention generally relates to ophthalmic examination apparatus, such as those used during an eye examination. More particularly, the invention relates to instrument arm assemblies used to position an examination instrument with respect to a patient.

BACKGROUND

During an eye examination, a series of tests are performed on a patient, who is typically seated in an examination chair. These tests can include an external examination of the eyes and surrounding tissues, tests to determine the acuteness or clearness of vision, examination of the pupils, and other examinations, tests or procedures pertaining to the eyes. Instruments are used during the eye examination and these instruments are typically retrieved from or stored on an associated instrument delivery stand positioned nearby the seated patient. For example, instrument delivery stands are known that include an instrument arm for presenting and positioning a table supporting an examination instrument in front of a patient. For example, a slit lamp machine may be supported on a table connected with an instrument arm, and is used by an eye doctor or other examiner to view different parts of the eye, including the cornea, the iris, the optic nerve, the retina, and the like.

Because of natural variations in the size and shape of patients, an instrument arm ought to have features providing position-adjusting capabilities in order to appropriately position an examination instrument with respect to a patient. For example, a child may be significantly shorter than an average-height adult, so an instrument arm should be able to position the examination instrument at a child-appropriate height. In addition, a heavyset patient will be positioned differently in an examination chair than a skinny patient, and an instrument arm should be able to position the examination instrument appropriately in either case.

Moreover, examination of wheelchair-bound patients presents other issues related to the presentation and positioning of examination instruments. In some circumstances, for example, a conventional examination chair must be moved to make room for patient in a wheelchair. An instrument arm should be able to position an examination instrument, such as a slit lamp machine, appropriately with respect to a wheelchair-bound patient. This may be challenging, however, if an examination room is not sufficiently large to easily accommodate the modifications necessary for the examination. For example, it may not be possible to completely remove a conventional examination chair, as they are typically very large and heavy. In other circumstances, the positional adjustability of the instrument arm may be insufficient to appropriately position the examination instrument with respect to a wheelchair-bound patient.

There is a need, therefore, for eye examination instrument arm assemblies and related devices that address one or more of the needs in the field of ophthalmic examination apparatus and provides for appropriate positioning of an examination instrument with respect to a patient.

SUMMARY OF THE INVENTION

According to one embodiment of the invention, an instrument arm assembly is provided for presenting an examination instrument to a seated patient. The instrument arm assembly includes an arm having an attachment assembly, an instrument supporting element for supporting the examination instrument and having an attachment assembly, and a linkage having first and second attachment assemblies. The instrument supporting element attachment assembly is pivotably connected with the linkage first attachment assembly, and the arm attachment assembly is pivotably connected with the linkage second attachment assembly.

According to another embodiment of the invention, a method is provided for adjusting the position of an instrument supporting element of an instrument arm assembly that further includes an arm, a linkage, and a support. The method includes rotating the instrument supporting element with respect to the linkage, rotating the linkage with respect to the arm, and rotating the arm with respect to the support.

According to another embodiment of the invention, an eye examination suite includes an instrument delivery stand, a chair positioned adjacent the stand for supporting a patient thereon, and an instrument arm assembly coupled with the instrument delivery stand. The instrument arm assembly includes an arm pivotably coupled with respect to an arm support and pivotable between a first position adjacent the chair and a second position away from the chair, a linkage pivotably coupled with the arm, and an an instrument supporting element pivotably coupled with the linkage and for supporting an examination instrument thereon.

Various additional features and advantages of the invention will become more apparent to those of ordinary skill in the art upon review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE ILLUSTRATIVE EMBODIMENTS

Referring now to the figures, an exemplary eye examination suite in accordance with the principles of the present invention is shown and is indicated generally by the numeral 10. The eye examination suite 10 is of the type used for examinations and includes an instrument delivery stand 12, a chair 14 for a patient to sit in, and a base 16. In the embodiment shown, the stand 12 and the chair 14 are connected through the base 16, but it will be appreciated that the present disclosure is applicable to other eye examination apparatus configurations, as well. During an eye examination, a patient would be seated in the chair 14 in a forward-facing direction, and an eye doctor or other practitioner would stand or be seated on a stool (not shown) generally in the region near the patient in the chair 14 and the stand 12.

Figure 1:
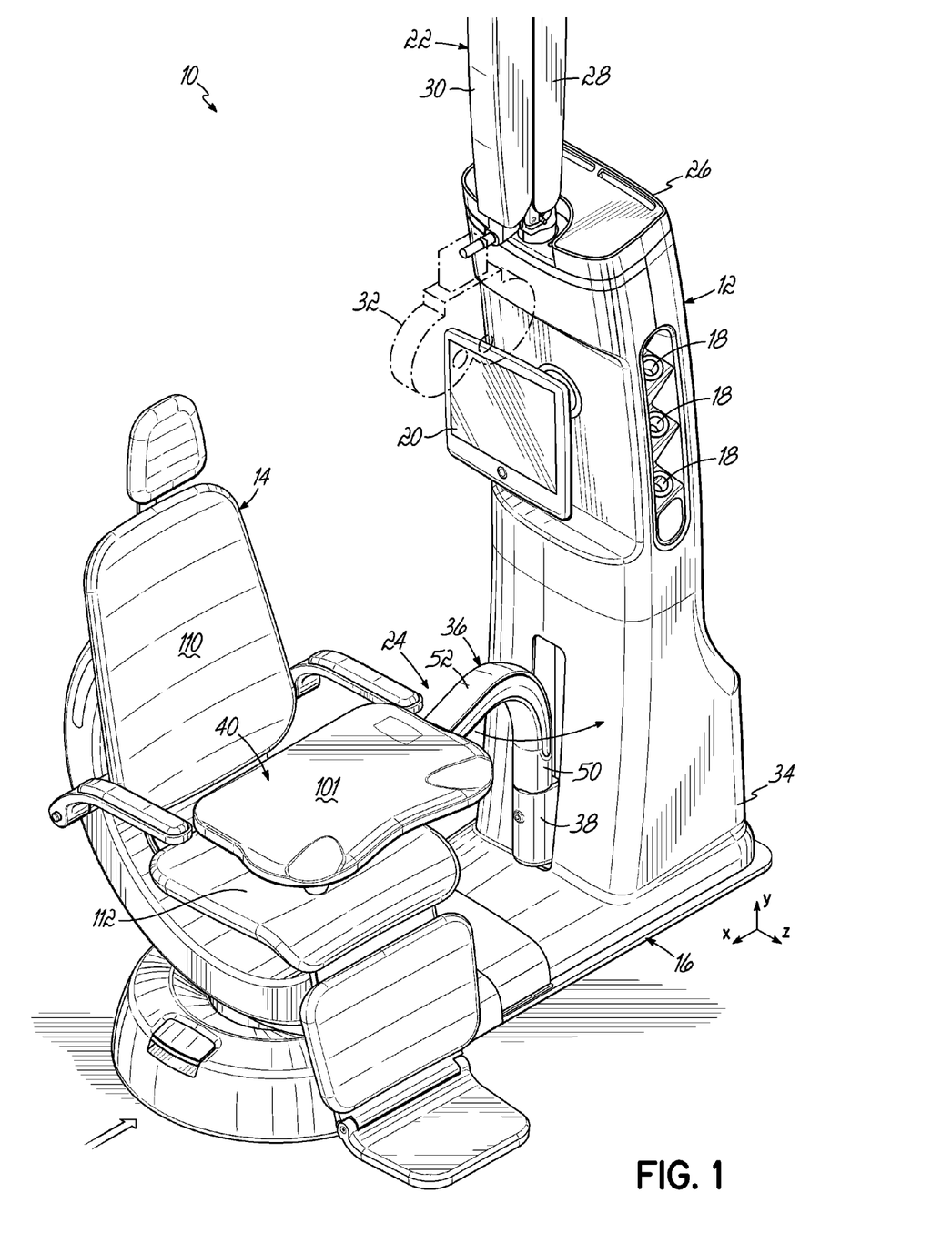
FIG. 1 is an isometric view of an eye examination suite.
Figure 2:
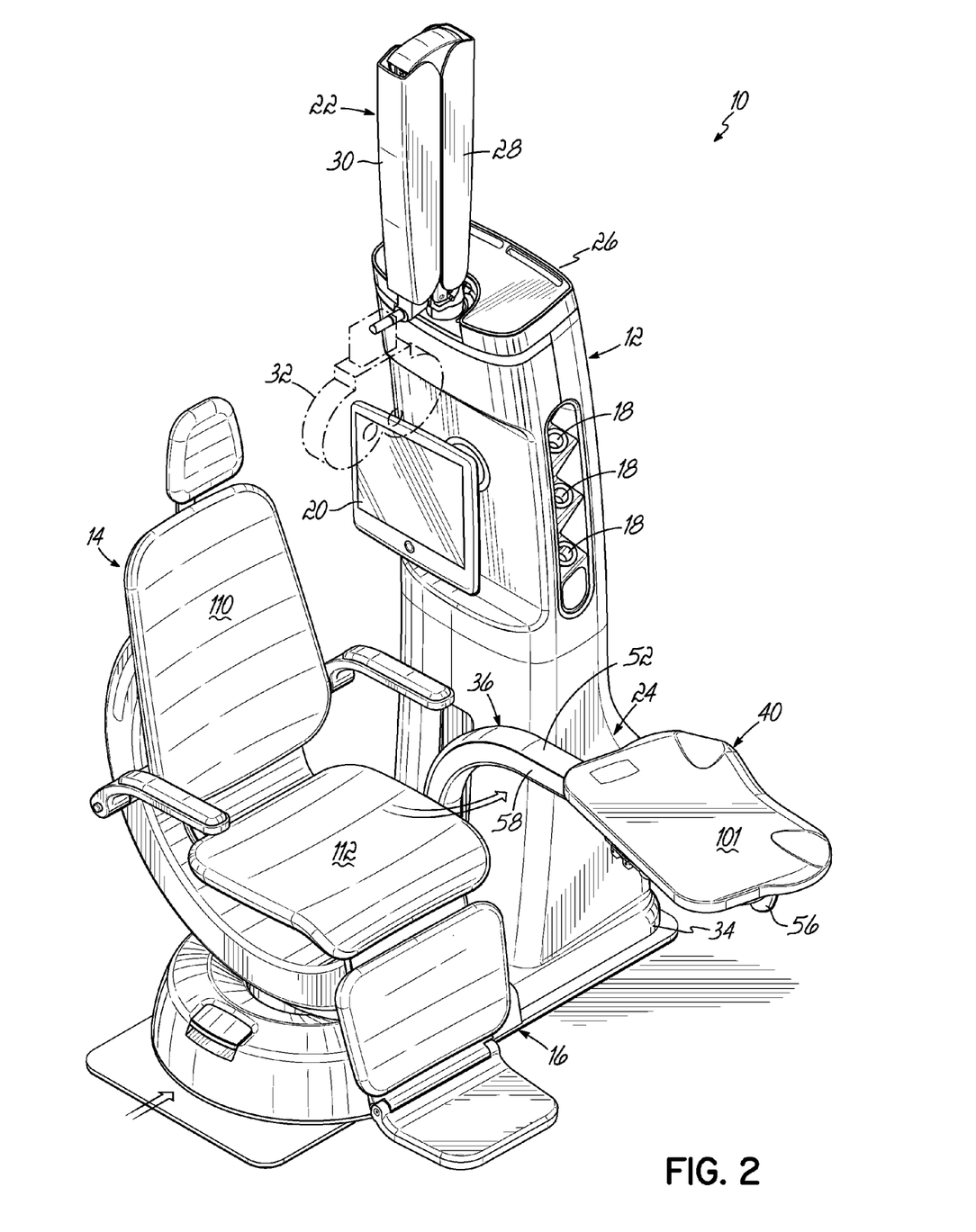
FIG. 2 is a further isometric view of the eye examination suite of FIG. 1, with the chair moved toward the instrument delivery stand and the lower instrument arm assembly rotated away from the chair.

As shown in FIG. 1, the stand 12 provides storage 18 for examination instruments, supports an information screen 20, and includes an upper instrument arm assembly 22 and a lower instrument arm assembly 24. The upper instrument arm assembly 22 extends from an upper region 26 of the stand 12 and includes a first arm portion 28, a second arm portion 30, and a phoropter 32. The first arm portion 28 is adjustably connected with the stand 12, and the second arm portion 30 is adjustably connected with the first arm portion 28. In addition, the phoropter 32 is adjustably connected with the second portion 30. Through these adjustable connections, the upper instrument arm assembly 22 is adjustable with respect to a seated patient and allows the physician or practitioner to position the phoropter 32 appropriately with respect to the patient's face and eyes as part of an eye examination. The upper instrument arm assembly 22 can also be placed into a stored position adjacent the stand 12, as shown in FIGS. 1 and 2.

Figure 3:
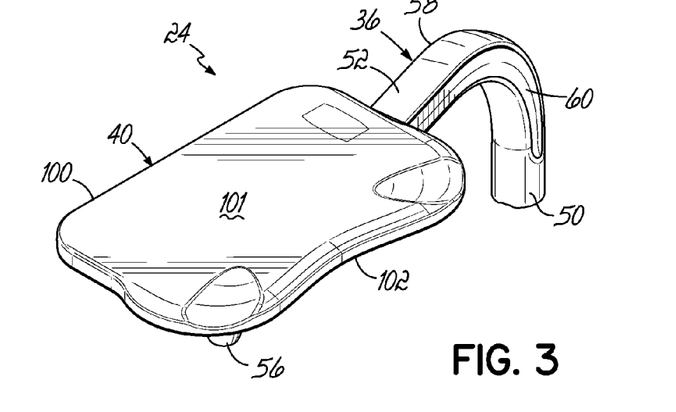
FIG. 3 is an isometric view of a portion of the lower instrument arm assembly shown in FIG. 1.
Figure 4:
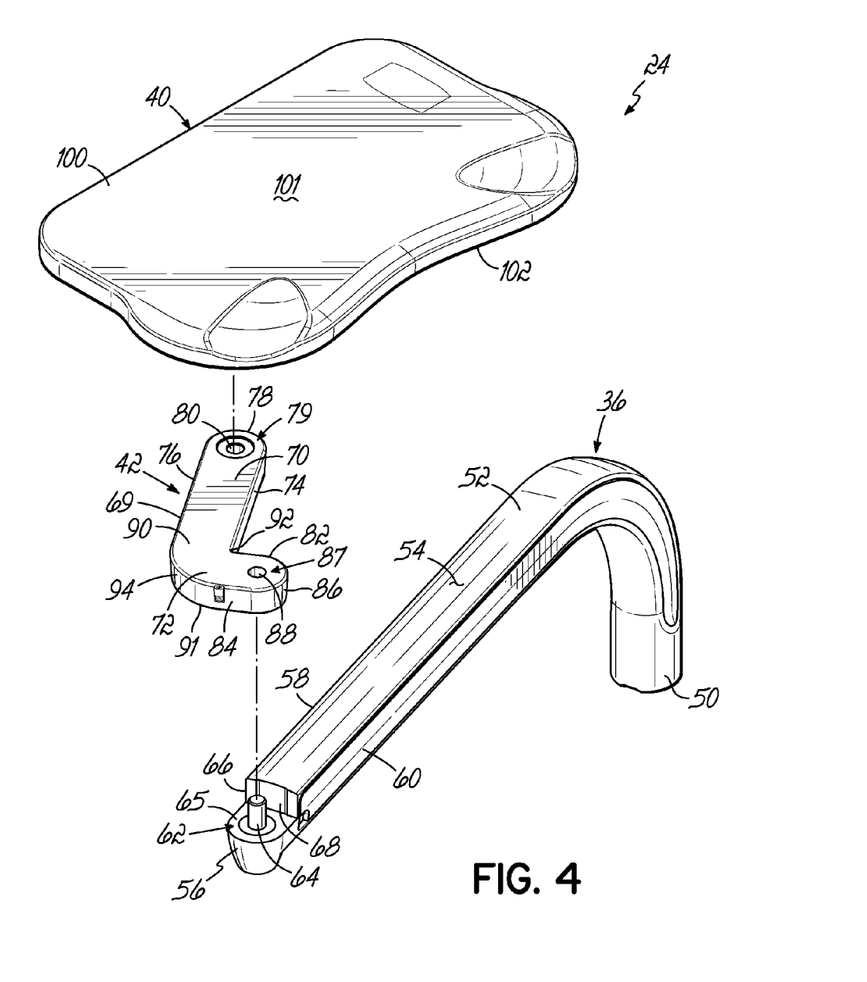
FIG. 4 is a disassembled view of the portion of the lower instrument arm assembly shown in FIG. 3.

The lower instrument arm assembly 24 extends from a lower region 34 of the stand 12 and includes an arm 36 extending upwardly from a support 38, an instrument supporting element (such as a table 40), and a linkage 42 (FIGS. 3 and 4). The arm 36 is adjustably connected with the support 38, and the table 40 is adjustably connected with the arm 36 by the linkage 42. For example, the arm 36 is pivotably rotatable with respect to the support 38, between positions adjacent (FIG. 1) and away (FIG. 2) from the chair 12. The adjustable connection between the arm 36 and the table 40 is discussed further, below. Optionally, the arm 36 may be raised or lowered with respect to the base 16, such as by raising or lowering the support 38. Through these adjustable connections, the lower instrument arm assembly 24 is adjustable with respect to a seated patient and allows the physician or practitioner to position the table 40 (or any other instrument supporting element) appropriately with respect to the patient as part of an eye examination.

With reference to FIGS. 1-4, the arm 36 of the lower instrument arm assembly 24 is further described. The arm 36 generally includes a first arm portion 50 that extends generally upwardly from the support 38 and a second arm portion 52 that extends generally outwardly from the first arm portion 50. The second arm portion 52 includes an upper surface 54 and terminates at a distal end 56. The second arm portion 52 includes a first side surface 58, which in some arrangements faces a patient seated in the chair 14, and a second side surface 60 generally opposite from the first side surface 58.

The arm 36 includes an attachment assembly 62 for adjustably connecting the arm 36 with the linkage 42. In the embodiment shown, the attachment assembly 62 includes a post 64 positioned generally near the distal end 56. In particular, the post 64 extends upwardly from a base 65 of a recessed portion 66 that is partially defined by a wall 68 that extends downwardly from the upper surface 54 and is spaced from the distal end 56. As will become apparent from the following description, the linkage 42 is adjustably connected to the arm 36 through the attachment assembly 62.

In the embodiment shown, the linkage 42 is substantially L-shaped when viewed from the top and includes a body 69 having a first leg portion 70 connected with a second leg portion 72. In the embodiment shown, the leg portions 70, 72 are generally perpendicular with one another, such as to have a dogleg shape. It will be appreciated, however, that the linkage 42 could alternatively have leg portions configured in various other non-perpendicular arrangements. In the embodiment shown, the second leg portion 72 has a major dimension that is smaller than the major dimension of the first leg portion 70, but it will be appreciated that various other length configurations for the leg portions 70, 72 could alternatively be used as may be desired.

The first leg portion 70 includes a first, interior, surface 74 and a second, exterior, surface 76. The interior and exterior surfaces 74, 76 are generally linear and opposite from one another and are connected on one end of the first leg portion 70 by a rounded surface 78. The first leg portion 70 further includes a first attachment assembly 79, which in the embodiment shown, includes a pivot bore 80 formed near the rounded surface 78. The pivot bore 80 may be a blind bore, a through-bore, a countersunk bore, or may have any other suitable configuration. The first attachment assembly 79 is used to connect the linkage 42 with the table 40.

The second leg portion 72 includes a first, interior, surface 82 and a second, exterior, surface 84. The interior and exterior surfaces 82, 84 are generally linear and opposite from one another and are connected on one end of the second leg portion 72 by a rounded surface 86. The second leg portion 72 further includes a second attachment assembly 87, which in the embodiment shown, includes a pivot bore 88 formed near the rounded surface 86. The pivot bore 88 may be a blind bore, a through-bore, a countersunk bore, or may have any other suitable configuration. The second attachment assembly 87 is used to connect the linkage 42 with the arm 36.

The interior surface 74 of the first leg portion 70 connects with the interior surface 82 of the second leg portion 72 at an inner transition region 92, which in the embodiment shown is a generally perpendicular angle. The exterior surface 76 of the first leg portion 70 connects with the exterior surface 84 of the second leg portion 72 at an outer transition region 94, which in the embodiment shown is generally curved.

The body 69 of the linkage 42 generally includes an upper surface 90 and an opposite lower surface 91.

Figure 6:
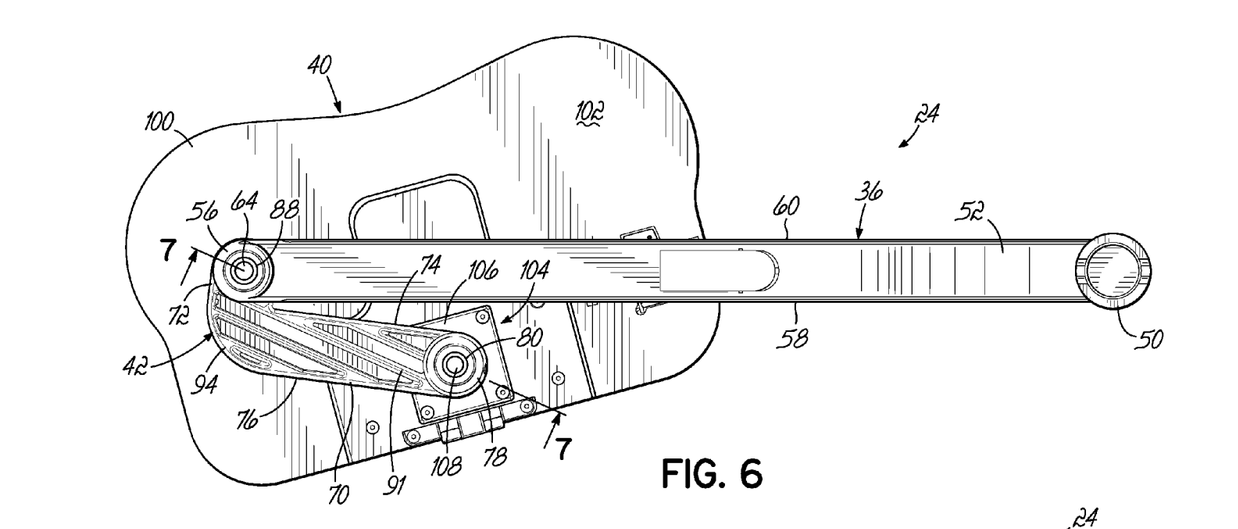
FIG. 6 is a bottom plan view of a portion of the lower instrument arm assembly.

The table 40 includes a body 100 having an upper surface 101, such as for supporting an examination instrument thereon, and a lower surface 102 disposed generally opposite from the upper surface 101. The table 40 also includes an attachment assembly 104, which in the embodiment shown includes a support bracket 106 attached with the body 100. A post 108 depends downwardly from the support bracket 106 (FIG. 6). The attachment assembly 104 provides structure for adjustably connecting the table 40 with the linkage 42. Of course, it will be appreciated that the post 108 may alternatively connect directly with, or be integral with, the body 100.

Figure 7:
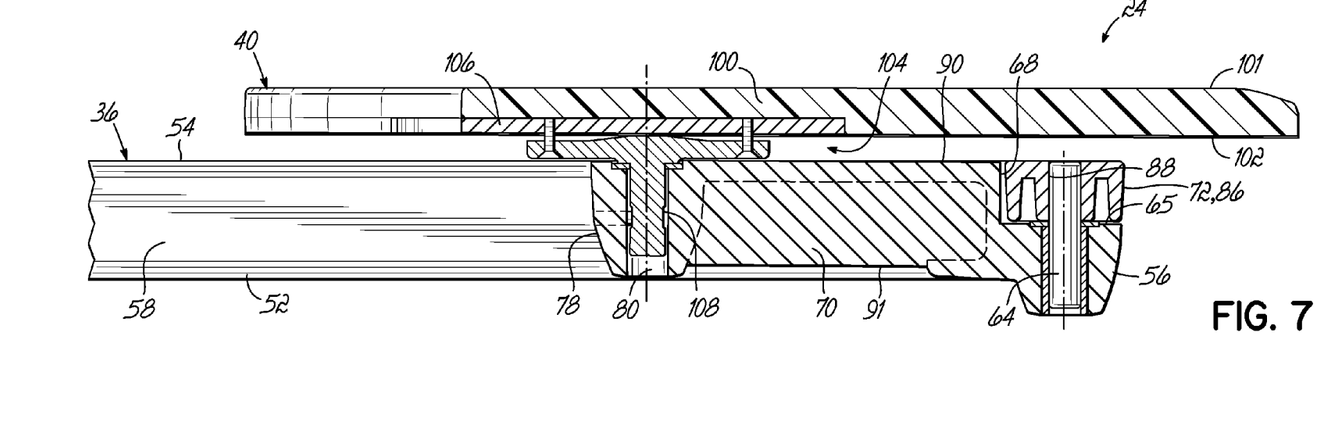
FIG. 7 is a cross-sectional view taken generally along line 7-7 in FIG. 6.

The various attachment assemblies 62, 79, 87, and 104 provide for the adjustable connection between the arm 36, the linkage 42, and the table 40. As shown in FIGS. 4 and 7, the attachment assembly 62 of the arm 36 is connected with the second attachment assembly 87 of the second leg portion 72 of the linkage 42. In particular, the pivot bore 88 of the second leg portion 72 is positioned onto the post 64 near the distal end 56 of the second arm portion 52 of the arm 36. The lower surface 91 of the linkage 42 rests on the base 65 of the arm 36. As shown in the figures, the shape of the wall 68 can be configured to relate to the shape of the linkage 42. In particular, the wall 68 can have a generally curved shape that corresponds with the rounded surface 86 of the second leg portion 72.

The attachment assembly 104 of the table 40 is connected with the first attachment assembly 79 of the first leg portion 70 of the linkage 42. In particular, the post 108 of the table 40 is positioned into the pivot bore 80 of the first leg portion 70 of the linkage 42.

Bearings or other rotation-assisting structure (not shown) can be incorporated into any of pivot bores 80, 88 or posts 64, 102. Further, any of the attachment assemblies 62, 79, 87, 104 can include structure for maintaining the connected relationship formed with another attachment assembly.

The linkage 42 is rotatably pivotable with respect to the second arm portion 52 of the arm 36, and the table 40 is rotatably pivotable with respect to the linkage 42. Accordingly, the table 40 is adjustable with respect to the arm 36, and this adjustment can be made to accommodate many patients, as will be described in further detail below.

The configuration of the disclosed attachment assemblies 62, 87 also provides for a low height profile configuration between the table 40 and the second arm portion 52 of the arm 36. In particular, because the second arm portion 52 includes the recessed portion 66, most, if not substantially all, of the body 69 of the linkage 42 can be positioned below the upper surface 54 of the second arm portion 52. As shown in FIG. 7, the upper surface 90 of the linkage 42 is generally aligned with the upper surface 54 of the second arm portion 52. Also, the configuration of the attachment assembly 104 of the table 40 allows the lower surface 102 of the table 40 to be closely positioned with respect to the upper surface 90 of the linkage 42. Consequently, the lower surface 102 of the table 40 can be closely positioned with respect to the upper surface 54 of the second arm portion 52, providing a low height profile where the table 40 connects with the arm 36.

Figure 5A:
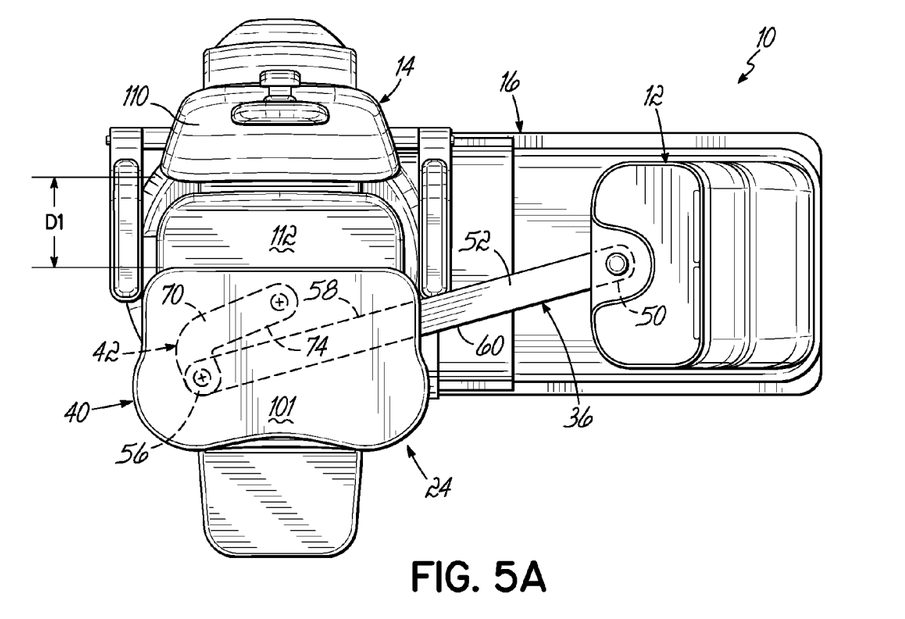
FIG. 5A is a top plan view of the eye examination suite shown in FIG. 1, with the lower instrument arm assembly in a first position.

Referring now to FIGS. 5A-D, various positions and arrangements for the lower instrument arm assembly 24 made possible by the linkage 42 will now be described. FIG. 5A depicts a first position where the table 40 is situated very near a back portion 110 of the chair 14, such as may be required by a child or slender patient. The distance between the back portion 110 and the table 40 is indicated at D1. In this arrangement, the second arm portion 52 of the arm 36 extends somewhat over a seat portion 112 of the chair 14, and the interior surface 74 of the first leg portion 70 is positioned closely to, but is not touching, the side surface 58 of the second arm portion 52. Also, the interior surface 82 of the second leg portion 72 is positioned generally opposite the wall 68 that partially defines the recessed portion 66 on the second arm portion 52 of the arm 36.

Figure 5B:
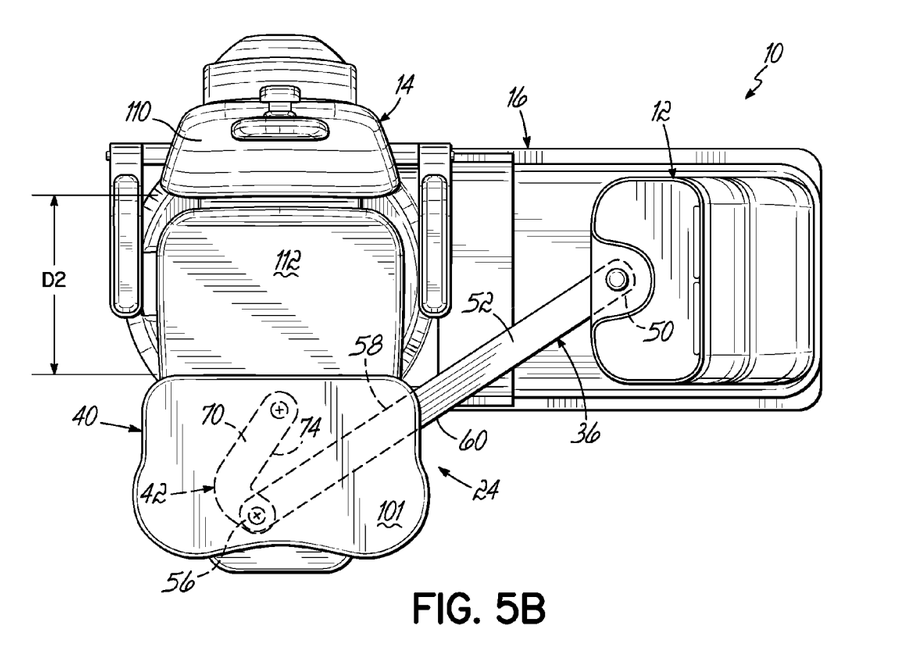
FIG. 5B is a top plan view similar to FIG. 5A, with the lower instrument arm assembly in a second position.

FIG. 5B depicts a second position where the table 40 is situated a greater distance from the back portion 110 than what is shown in FIG. 5A. The distance between the back portion 110 and the table 40 is indicated at D2. In this arrangement, the second arm portion 52 barely extends over the seat portion 112, and the interior surface 74 is spaced from the side surface 58 more than the arrangement shown in FIG. 5A, with the table 40 having been rotated somewhat with respect to the linkage 42 and with the linkage 42 having been rotated somewhat with respect to the second arm portion 52 of the arm 36. Also, part of the interior surface 82 and part of the rounded surface 86 of the second leg portion 72 are positioned generally opposite the wall 68. In this second position, the arm 36 is pivoted so the second arm portion 52 is positioned further from the back portion 110 compared to the position of the second arm portion 52 in the configuration depicted in FIG. 5A.

Figure 5C:
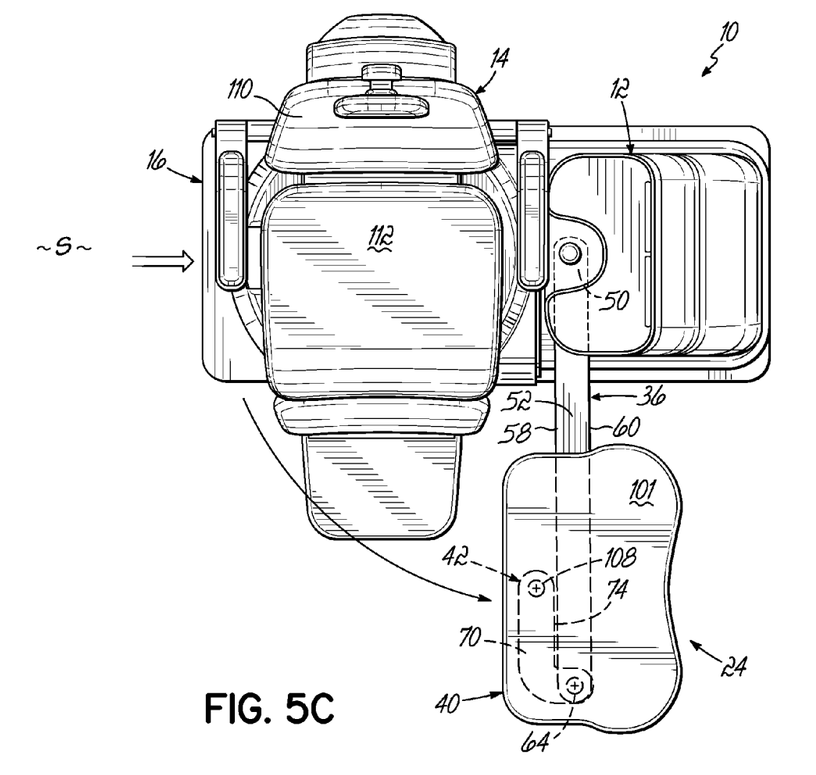
FIG. 5C is a top plan view similar to FIG. 5A, with the lower instrument arm assembly in a third position.

FIG. 5C depicts a third position, where the arm 36 is rotated so the second arm portion 52 is away from the chair 14. In this arrangement, the interior surface 74 of the first leg portion 70 abuts the side surface 58 of the second arm portion 52, and the interior surface 82 of the second leg portion 72 abuts the wall 68 of the second arm portion 52. Also, the interior surface 82 of the second leg portion 72 is positioned generally opposite the wall 68.

Figure 5D:
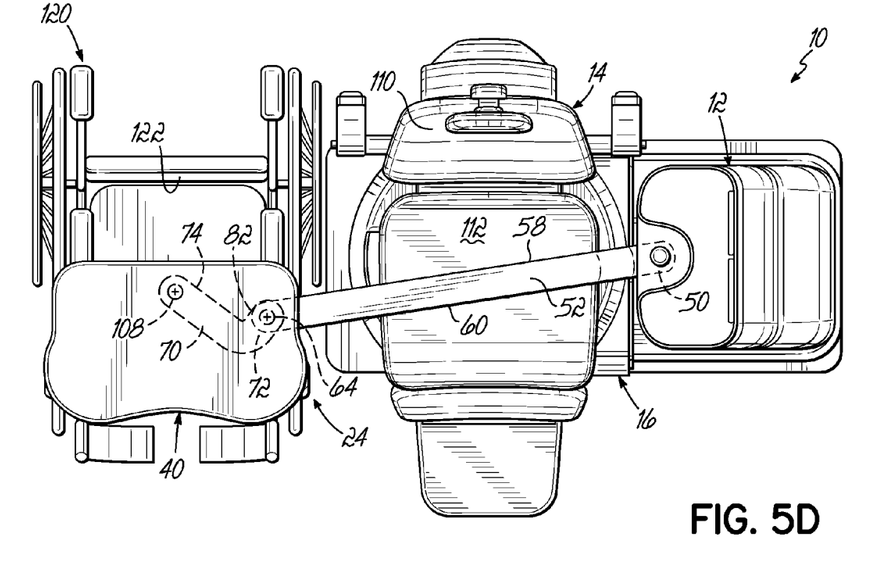
FIG. 5D is a top plan view of the eye examination suite shown in FIG. 1, with the chair moved toward the instrument delivery stand and a wheelchair situated in an examination position, with the lower instrument arm assembly in a fourth position.

FIG. 5D depicts a fourth position where the table 40 is situated over a wheelchair 120, such as when a wheelchair-bound patient is undergoing an eye examination. The chair 14 has been moved nearer the stand 12 in a direction transverse to the forward-facing direction in order to situate the wheelchair 120 in a position for a wheelchair-bound patient to be examined. In this arrangement, the table 40 is rotated with respect to the linkage 42 and the linkage 42 is rotated with respect to the second leg portion so that the interior surfaces 74 and 82 generally open toward a back support 122 of the wheelchair 120. Also, the rounded surface 86 of the second leg portion 72 is positioned generally opposite the wall 68. In this fourth position, the arm 36 is pivoted so the second arm portion 52 is appropriately spaced from the back support 122, which in the figure is more like what is shown in FIG. 5A than in FIG. 5B. Also, the second arm portion 52 extends generally beyond the chair 14, which, again, has been moved nearer the stand 12.

The linkage 42, therefore, provides adjustable positioning of the table 40, such as to accommodate differently-sized patients and patients in wheel chairs. As shown in FIG. 5D, the linkage 42 provides an extended reach for the table 40 when the first leg portion 70 is rotated substantially away from the second arm portion 52. This is advantageous for presenting the table 40, and any instruments thereon, to a wheel-chair bound patient.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. An instrument arm assembly for presenting an examination instrument to a seated patient, comprising:

an arm having an arm attachment assembly, the arm having an upper surface and a lower surface, a table having an upper surface for supporting the examination instrument and a lower surface having a table attachment assembly extending therefrom, and a linkage having a linkage body, an upper surface and a lower surface, wherein the upper surface of the linkage is generally aligned with the upper surface of the arm to create a substantially planar surface, wherein the linkage body has a first leg portion rigidly connected and transverse to a second leg portion preventing the first leg portion from rotating relative to the second leg portion, the first portion having a first linkage attachment assembly and the second leg portion having a second linkage attachment assembly, and wherein the table attachment assembly is fastened to the lower surface of the table and further pivotably connected with the first linkage attachment assembly, and the arm attachment assembly is pivotably connected with the second linkage attachment assembly at a single pivot point allowing the linkage to increase the reach of the table when in a first angular orientation and decrease the reach of the table when in a second angular orientation;

wherein an interior surface of the first leg portion is configured to abut a side surface of the arm when the table is positioned at a third angular orientation, the arm attachment assembly being positioned underneath the lower surface of the table when the table is in the third angular orientation, and wherein the lower surface of the table is positioned above the upper surface of the arm and the upper surface of the linkage.

2. The instrument arm assembly of claim 1, wherein the first linkage attachment assembly includes a first bore formed in the linkage body, and the table attachment assembly includes post extending into the first bore of the linkage body.

3. The instrument arm assembly of claim 2, wherein the table includes a support bracket, the post extending from the support bracket.

4. The instrument arm assembly of claim 1, wherein the second linkage attachment assembly includes a second bore formed in the linkage body, and the arm attachment assembly includes a post extending in the second bore of the linkage body.

5. The instrument arm assembly of claim 4, wherein the arm includes a recessed portion having a base, the post extending from the base.

6. The instrument arm assembly of claim 1, wherein the first and second leg portions are perpendicular with one another.

7. The instrument arm assembly of claim 1, wherein the first leg portion has a major dimension greater than a major dimension of the second leg portion.

8. The instrument arm assembly of claim 1, wherein the first leg portion of the linkage body is generally parallel to the arm in the second angular orientation.

9. A method of adjusting the position of a table having an upper surface and a lower surface, the table being part of an instrument arm assembly that further includes:

an arm having an upper surface and a lower surface, a linkage having an upper surface and a lower surface, wherein the upper surface of the linkage is generally aligned with the upper surface of the arm to create a substantially planar, uniform surface and wherein the lower surface of the table is positioned above the upper surface of the arm and the upper surface of the linkage and is configured to be positioned with respect to the substantially planar, uniform surface to provide a low height profile where the table connects with the arm, and a support, the method comprising:

rotating the table with respect to the linkage at a table attachment assembly fastened to the lower surface of the table and about a first pivot point of the table attachment assembly, wherein the linkage includes a linkage body having a first leg portion rigidly connected and transverse to a second leg portion preventing the first leg portion from rotating relative to the second leg portion, rotating the linkage with respect to the arm about a second pivot point and into a first angular orientation that increases the reach of the table, rotating the linkage with respect to the arm about the second pivot point and into a second angular orientation that decreases the reach of the table, and rotating the arm with respect to the support;

wherein an interior surface of the first leg portion is configured to abut a side surface of the arm when the table is positioned at a third angular orientation, the arm attachment assembly being positioned underneath the lower surface of the table when the table is in the third angular orientation.

10. The method of claim 9, wherein rotating the linkage includes moving the first leg portion with respect to the arm.

11. The method of claim 10, wherein rotating the linkage includes rotating a bore in the linkage around a post on the arm.

12. The method of claim 9, wherein rotating the table includes rotating a post on the table in a bore in the linkage.

13. The method of claim 9, wherein the rotating the table with respect to the linkage further comprises rotating the table such that the first leg portion of the linkage body is generally parallel to the arm.

14. An eye examination suite comprising:

an instrument delivery stand, a chair positioned adjacent the stand for supporting a patient thereon, and an instrument arm assembly coupled with the instrument delivery stand and comprising an arm pivotably coupled with respect to an arm support and pivotable between a first position adjacent the chair and a second position away from the chair, a linkage pivotably coupled with the arm at a single pivot point, and a table pivotably coupled with the linkage, the table having an upper surface and a lower surface and a table attachment assembly fastened to the lower surface of the table, wherein the arm and the linkage each have an upper surface and a lower surface, the upper surfaces of the arm and linkage being generally aligned to create a substantially planar, uniform surface, and wherein the lower surface of the table is positioned above the upper surface of the arm and the upper surface of the linked and is configured to be positioned with respect to the substantially planar, uniform surface to provide a low height profile where the table connects with the arm, wherein the linkage includes a linkage body having a first leg portion rigidly connected and transverse to a second leg portion preventing the first leg portion from rotating relative to the second leg portion, the first leg portion being pivotably coupled with the table attachment assembly and the second leg portion being pivotably coupled with the arm; and wherein an interior surface of the first leg portion is configured to abut a side surface of the arm when the table is positioned at a third position, the arm attachment assembly being positioned underneath the lower surface of the table when the table is in the third position.

15. The eye examination suite of claim 14, wherein the table is moveable between at least a first position wherein the coupling between the linkage and the instrument delivery stand is generally adjacent the arm and a second position wherein the coupling between the linkage and the instrument delivery stand is generally distal from the arm.

16. The eye examination suite of claim 14, wherein the first leg portion of the linkage body is generally parallel to the arm in the second position away from the chair.

* * * * *